United States Patent [19]

Deloison et al.

[11] 4,355,428
[45] Oct. 26, 1982

[54] SURGICAL PROSTHESIS WITH GRAINY SURFACE

[75] Inventors: Victor Deloison, Courbevoie; Gilbert Pottier, Calvados, both of France

[73] Assignee: S.A. Benoist Girard & Cie, Val de Marne, France

[21] Appl. No.: 91,165

[22] Filed: Nov. 5, 1979

Related U.S. Application Data

[63] Continuation of Ser. No. 810,772, Jun. 28, 1977, Pat. No. 4,819,984.

[30] Foreign Application Priority Data

Jul. 2, 1976 [FR] France .............................. 76 20297

[51] Int. Cl.$^3$ .............................................. A61F 1/20
[52] U.S. Cl. .................................................. 3/1.91
[58] Field of Search ...................... 3/1.9, 1.911, 1.912, 3/1.913, 1.91; 433/172, 173, 175, 176, 180; 128/92 R, 92 BC, 92 C, 92 CA, 92 G

[56] References Cited

U.S. PATENT DOCUMENTS

| | | | |
|---|---|---|---|
| 2,258,207 | 10/1941 | Irwin | 433/176 |
| 2,599,044 | 6/1952 | Brennan | 433/173 |
| 2,936,490 | 5/1960 | Mason | 433/180 X |
| 3,375,582 | 4/1968 | Myerson | 433/176 X |
| 3,729,825 | 5/1973 | Linkow et al. | 433/176 |
| 3,760,502 | 9/1973 | Hirsch | 433/176 X |
| 3,826,241 | 7/1974 | Bucalo | 433/173 X |
| 3,829,972 | 8/1974 | Pasqualini et al. | 433/176 |
| 3,855,638 | 12/1974 | Pilliar | 433/173 X |
| 3,905,047 | 9/1975 | Long | 3/1.9 |

FOREIGN PATENT DOCUMENTS

| | | | |
|---|---|---|---|
| 328360 | 1/1920 | Fed. Rep. of Germany | 433/173 |
| 2237598 | 2/1974 | Fed. Rep. of Germany | 433/176 |
| 2421951 | 11/1975 | Fed. Rep. of Germany | 433/176 |
| 2194123 | 2/1974 | France | 3/1.9 |
| 1305478 | 1/1973 | United Kingdom | 433/173 |

OTHER PUBLICATIONS

"The Dental Laboratory", Official Publication of the Association of German Dental Technician's Guilds, 6-14-65, p. 239.

*Primary Examiner*—E. H. Eickholt
*Attorney, Agent, or Firm*—Connolly and Hutz

[57] ABSTRACT

The invention relates to a process for manufacture of parts having a grainy surface and to parts obtained by this process. The process comprises making a rough wax pattern of the desired part, applying fusible particles to the surface of said pattern, obtaining a refractory mold from said pattern, and casting a material in the mold to form the finished part after removal of the mold. The resulting part has a grainy surface.

The invention applies in particular to the manufacture of stems of articulating prostheses to be inserted into bone without addition of cement.

4 Claims, 16 Drawing Figures

SURGICAL PROSTHESIS WITH GRAINY SURFACE

This application is a continuation of application Ser. No. 810,772 now U.S. Pat. No. 4,819,984 filed June 28, 1977.

BACKGROUND OF THE INVENTION

The present invention relates to a process for manufacture of a part having an irregular surface, more specifically a grainy surface. It relates likewise to a part obtained by such process.

In its most general form, the invention applies to the manufacture of any part intended to be inserted in a holding member with which it then forms an integral body, the resulting assembly being rigid and behaving as though it were made of one piece. It is known that the mechanical endurance (resistance to stresses, shape stability, etc.) of such an assembly, when its component parts are subjected to various forces, depends almost entirely on the quality of the anchorage of the inserted part in the holding member. Such is the case in particular for bone prostheses, more specifically joint prostheses. Joint prostheses comprise firstly an anchorage portion (generically referred to as the stem) inserted in the medullary canal of the holding bone after ablation of the defective bone end and secondly an active portion protruding from the holding bone and intended to cooperate with the complementary bone end of the joint.

The relative movements of the bones exert great forces on the prosthesis, and if the retention of the stem in the holding bone is imperfect, play may result between the prosthesis and the holding bone, with danger of serious accident, in particular by fracture of the prosthesis.

To avoid accident of this kind, the anchorage of a prosthesis in the holding bone receives very careful attention. The most widespread anchorage technique consists of retaining the pin in the medullary canal of the holding bone by means of a special cement.

This technique, however, involves disadvantages inherent in the use of a cement. Specifically:

1. The cement is a foreign body that may in the long run injure the bony tissue, in particular by impeding the process of regeneration. 2. Furthermore, and more seriously, because in order to provide a good anchorage there must be a relatively thick layer of cement between the stem and the walls of the canal excavated in the bone, the canal in the bone must be made larger in diameter than the cross section of the stem, thereby of course rendering the bone more fragile throughout the length of the canal. Moreover, if the prosthesis must eventually be replaced, it will be necessary to excavate the bone again, further reducing its strength and making any additional operations impossible.

To overcome there disadvantages, a technique of anchoring the prosthesis has recently been proposed characterized by elimination of the use of cement, the retention of the prosthesis in the bone being achieved by regeneration of bony tissue around and over the prosthesis, which is then positively embedded.

Such a technique clearly offers substantial advantages not only on the strictly medical level (omission of the cement as a foreign body, promotion of recalcification, less injury to the holding bone) but also on the levels of economy and facility of use.

However, this technique requires that the surface of the portion of the prosthesis that is inserted in the bone have properties ensuring a good mechanical bond between bone and prosthesis.

Classic stems of prostheses with smooth surfaces will not serve to make as satisfactory a bond as is required. To meet this difficulty, new stems have been proposed having an irregular surface produced by superficial acid attack, producing a multitude of irregular alveoli on the surface of the stem. It will be realized that such an irregular surface will serve for satisfactory retention of the prosthesis in the bone, since the bony tissue, as it is reconstituted, will fill the alveoli and form a multiplicity of projections entering the prosthesis in substantially radial directions.

Consequently, the bone itself will receive and absorb the stresses exerted on the prosthesis, and as a result the risk of detachment incurred by cemented prostheses is practically eliminated.

However, the irregularly surfaced prostheses currently proposed have, apart from an unpleasant pitted texture, the threefold disadvantage that:

(a) The mechanical strength of the stem is reduced because its thickness is locally dimished;
(b) Since the acid attack is irregular, zones of fragility occur at some of the walls between alveoli, with danger of superficial crumbling at some points on the stem, and consequently an uneven anchorage;
(c) The operation of acid attack causes an undesirable loss of material, especially in the case of prostheses made out of costly alloys.

SUMMARY OF THE INVENTION

A novel article of manufacture, a part having a grainy surface characterized in that said part presents externally a multitude of particles cast in one piece with the body of the part, has been discovered.

The present invention comprises also a novel bone prosthesis part intended to be fixed without cement in a recess made in a bone of the human or animal skeleton, characterized in that the portion of said part intended to be placed in the bone recess has an outer surface furnished with a multiplicity of particles leaving interstitial spaces between them to provide a positive anchorage of bony tissue in the prosthesis.

Additionally, the present invention includes a novel process for the manufacture of the above, and other, parts having a grainy surface which comprises:

(a) preparing a rough pattern of the part from a material capable of existing in the solid state and the liquid state, said rough pattern when finished being in the solid state;

(b) applying particles likewise of a material capable of existing in the solid state and the liquid state and causing them to adhere to the surface of said rough pattern, said particles being in the solid state at the moment of application;

(c) covering the resulting pattern from step (b) with a layer of refractory material to form a rigid shell of said refractory material;

(d) convering the totality of the material or materials constituting said pattern resulting from step (b) to the liquid state, and removing said material or materials to obtain a refractory mold;

(e) casting the molten material of which the finished part is to be constituted in said refractory mold; and (f) removing said refractory mold.

DETAILED DESCRIPTION OF THE INVENTION

The present invention comprises a process for the manufacture of parts having an irregular surface, in particular prostheses, eliminating the disadvantages described above in the "Background of the Invention" section. While the invention has been conceived specifically for making prostheses, it will be understood that it may be applied instead to the production of other kinds of parts intended to be anchored in a holding member, whether such anchorage is effected with or without addition of an intermediate material such as cement.

Incidentally, while in its specific form the present invention relates to the construction of prostheses intended for insertion in bone without use of cement, it will be understood that there is no obstacle to the use of prostheses made according to said invention in the conventional technique of fixation with cement, the irregular surface of the portion of the prostheses that is placed in the bone lending itself naturally to an improvement of cohesion between cement and prosthesis.

According to the present invention, and contrary to the prior art, it is proposed that a part with a nonsmooth surface, more specifically with a grainy surface, be obtained directly by casting.

It will be seen at once that this procedure serves among other things:

To eliminate any process of surface attack on the part by chemical or physical means, such processes being in general costly and necessitating either difficult handling of dangerous products (chemical) or costly and bulky equipment (mechanical);

To obtain a practically constant depth, over the entire surface of the part, of the zone of irregularity, thus providing a good homogeneity of anchorage of the part in the bone.

Finally—and this is an important difference—whereas by the process of acid attack the initial part has a smooth surface in which the acid produces small cavities, the surface of parts of the present invention consists of a multitude of projections cast integrally with the body of the part.

To fix the applied particles to the rough pattern, the surface of the latter is preferably rendered adhesive either by superficial softening, by wetting with a solution suitable for the material of the pattern, or by coating the pattern, for example by means of a brush, with an adhesive material such as a commercial glue.

Of course, without departing from the scope of the invention, one might render only the surfaces of the particles adhesive, or both the surfaces of the particles and that of the pattern. However, the preferred process comprising rendering only the surface of the pattern adhesive has the advantage of permitting better control of the final state of the surface of the part, because handling of the particles is avoided, and in the case of use of a wetting solution or an adhesive, the formation of local excess thicknesses of adhesive materials that might cause them to run over the particles is thereby prevented.

Specifically, the particles are applied to the pattern for example by manual or mechanical sprinkling so that they leave interstices between them. Furthermore, although the particles may be of any regular or irregular shape, it will be preferable to adopt the use of particles approximately in the shape of spherules, because this has been found to be the most favorable shape both to impart an agreeable texture to the final surface of the part and to ensure that, without special precautions in placement of the particles on the pattern, a surface most favorable to penetration and anchorage of bony tissue in the superficial zone of the prosthesis will be obtained. In fact, the use of spherules will permit formation, in the interstitial spaces left between them, of bony "peduncles" wider at the end than at the shank, preventing any radial displacement between bone and prosthesis.

Specifically, the rough pattern will preferably be made of mineral wax, the type of wax used being that ordinarily employed for lost wax casting.

The rough pattern may be made in a mold bearing a hollow replica of the part to be obtained with smooth surfaces. In other words, the rough pattern obtained will itself have smooth surfaces, the particles being afterwards spread over the smooth surfaces in the manner explained above.

The particles may be of any suitable material, such as wax or other soluble or fusible material. Thus in particular, according to a specific form of the invention, sized particles of plastic material will preferably be used, more specifically balls of polystyrene.

The layer of refractory material may be applied to the resulting pattern by the conventional process consisting of successive baths in a silica-silicate solution and sprinkling with silica-silicate powder after each bath.

Finally, in case fusible materials are used, such as wax or plastic, to make the rough pattern and the particles, said materials may be eliminated to make the refractory mold in the conventional manner by heating.

The present invention relates likewise, as a novel article of manufacture, to a part having a grainy surface, characterized by externally bearing a multitude of particles cast in one piece with the body of the part.

The particles are preferably spaced apart to leave interstitial spaces between them, which is particularly desirable when the part is the anchorage portion of a bone prosthesis, because the bone being reconstituted can occupy the said interstitial spaces, forming a multiplicity of points of anchorage.

Advantageously, the interstitial space between two neighboring particles will not be constant throughout the height of the particles, and not smallest at the base of the particles where they attach to the body of the part.

The preferred shape of the particles, to meet the specifications above, is the spherical shape.

By way of example but not of limitation, the process of the invention and a prosthesis thereby obtained will now be described with reference to the accompanying drawings, in which:

FIG. 4b shows a sectional detail, much enlarged, of FIG. 4a.

Figure 9:
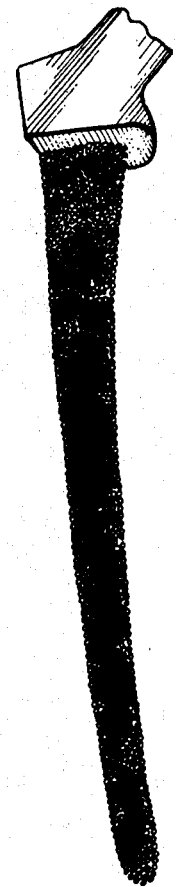
FIG. 9 shows the casting obtained.
Figure 9A:
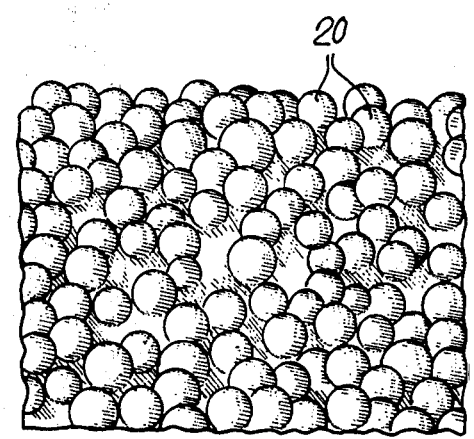

FIG. 9a, in much enlarged external view, shows the surface of the part of FIG. 9.

Figure 9B:
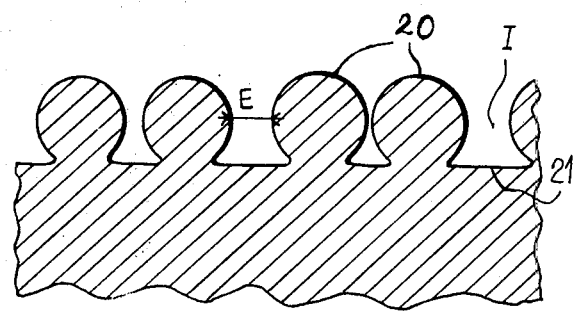

FIG. 9b is a radial section, to a large scale, of a portion of the surface of the part of FIG. 9.

In the following, the process of the invention will be described, by way of example, as applied to the production of the femoral portion of a total hip prosthesis, that is to say, the portion of the prosthesis intended to be inserted in the femur.

Figure 1:
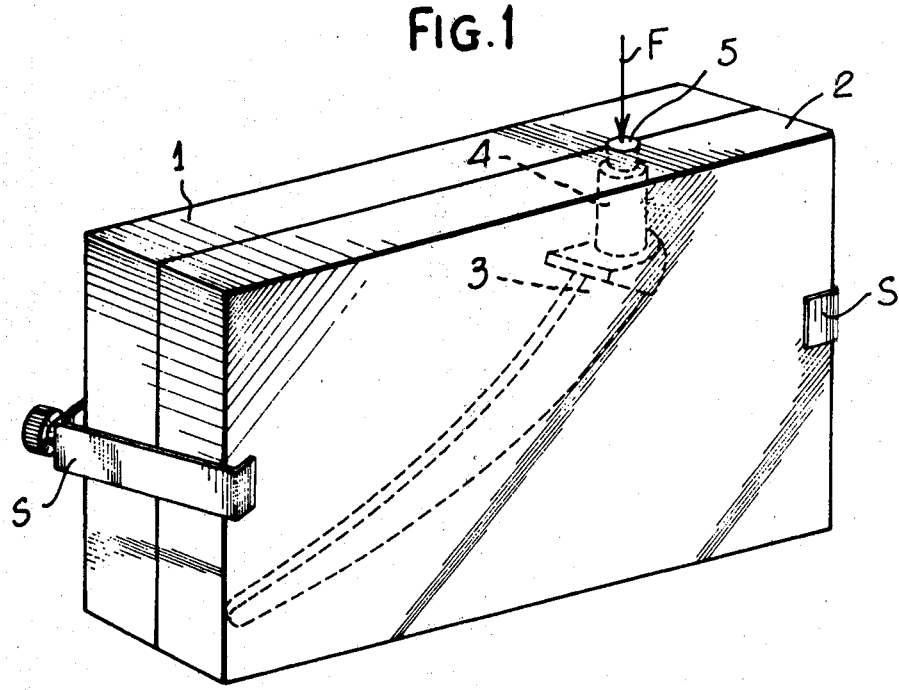
FIG. 1 is a perspective view of a mold used to mold the rough wax pattern.
Figure 1A:
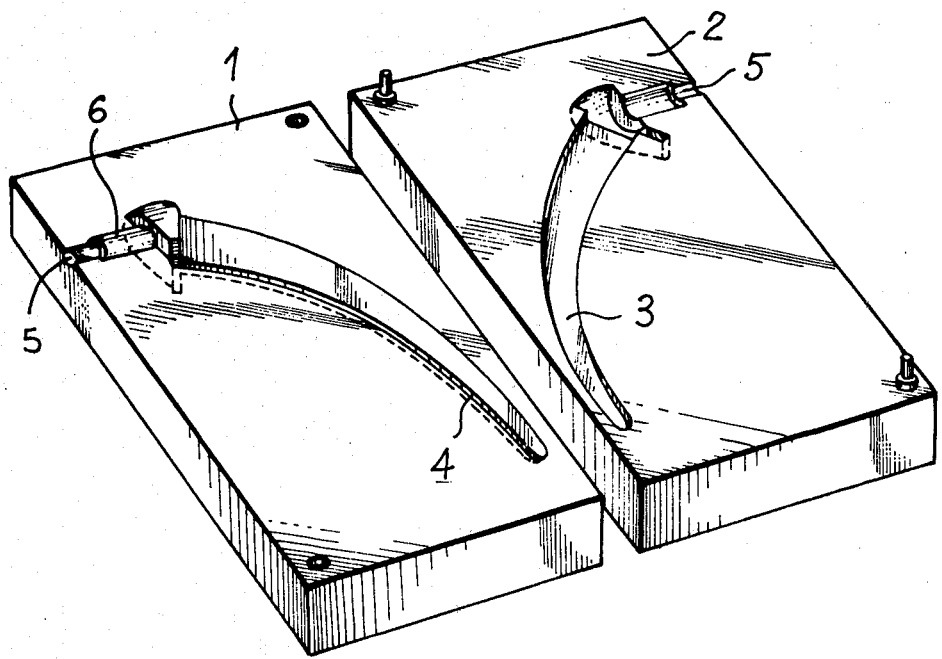
FIG. 1a is a view similar to FIG. 1, after the rough pattern has been molded, with the mold opened.

First a conventional mold is made like that shown in FIGS. 1 and 1a. This mold is in two parts 1 and 2, and in each part a hollow half-replica 3, 4 of the rough pattern to be obtained is fashioned, so that when the mold is closed, by clapping one part (1 or 2) over the other, the half-replicas 3 and 4 make a cavity the size and shape of the final rough pattern to be obtained. When the mold is closed with a conventional closing means S, the cavity formed by the half-replicas 3 and 4 communicates with the outside through a runner 5 into which is poured, following the arrow F of FIG. 1 into the mold, the material intended to make the rough pattern. In the example shown, ordinary mineral wax for molding by the so-called lost wax process is used, in particular a wax sold under the designation "L 115" by the firm of La Ceresine.

However, material other than wax may be used, for example plastic materials or mercury.

Of course, to allow it to be poured into the closed mold 1-2, the wax is heated to bring it into liquid or pasty form.

Figure 2:
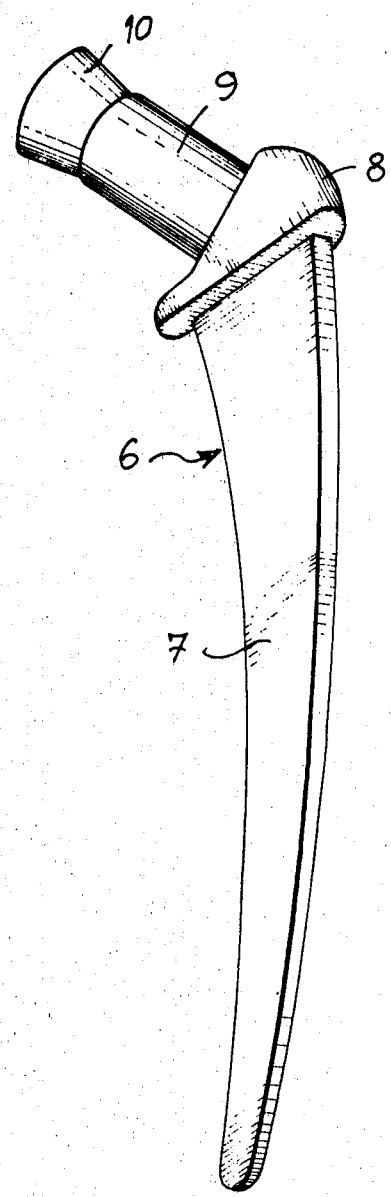
FIG. 2 shows the rough wax pattern extracted from the mold.

When the mold is filled, the wax is allowed to cool, solidifying it again, and the mold is opened as seen in FIG. 1a. Then a rough pattern 6 of wax is obtained, which is removed from the mold and has the appearance shown in FIG. 2. This rough pattern has a portion 7 (to form the stem intended for insertion in a recess made in the femur), a portion 8 (to form the seat of the prosthesis on the head of the femur), a portion 9 (to form the neck of the prosthesis) and a portion 10 (the blank for a portion of the spherical head of the prosthesis).

All of the following is concerned exclusively with operations performed on portion 7 of the rough pattern, which operations alone pertain to the invention.

After removing the rough wax pattern from the mold, a conventional operation of stabilization is performed to obtain proper endurance of the pattern during subsequent steps of treatment and to avoid any dimensional variations. This stabilization operation consists of leaving the pattern alone for at least 24 hours in a room conditioned to 20° C.

Figure 3:
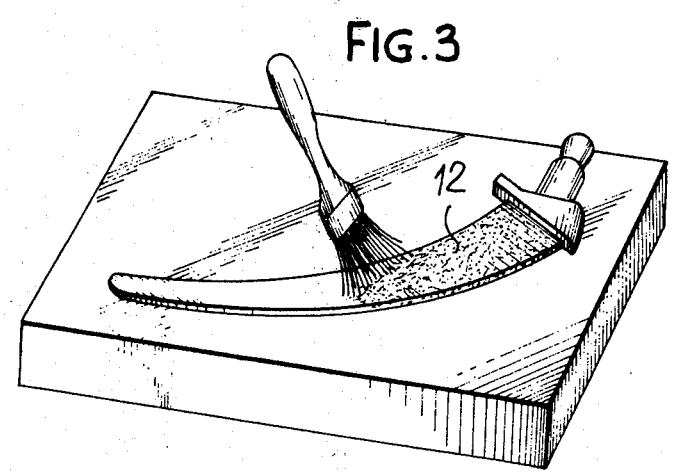
FIG. 3 shows the step of applying a layer of glue to the surface of the rough pattern.

As is seen in FIG. 3, a layer of commercial glue 12 is then applied, for example with a brush, to the entire surface of the portion 7 of the pattern. Of course the portion 7 may be rendered superficially adherent by any other suitable means.

Figure 4A:
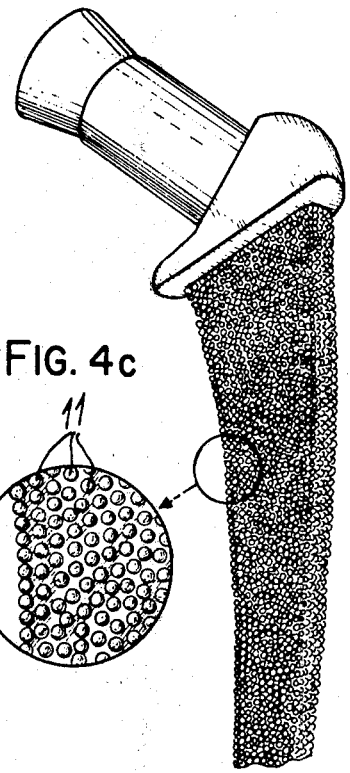
FIG. 4a shows the resulting pattern furnished with its balls of plastic material.
Figure 4C:
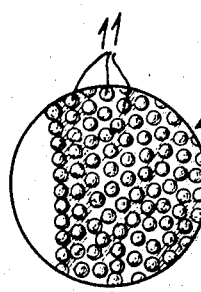
FIG. 4c shows a sectional detail of FIG. 4a but of lesser enlargement than FIG. 4b.
Figure 4B:
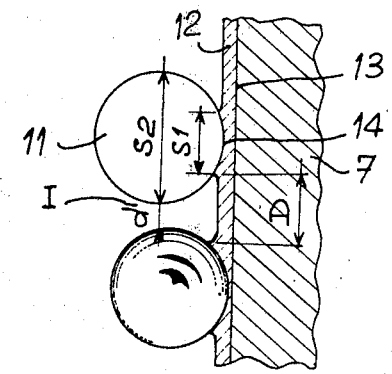
Figure 4:
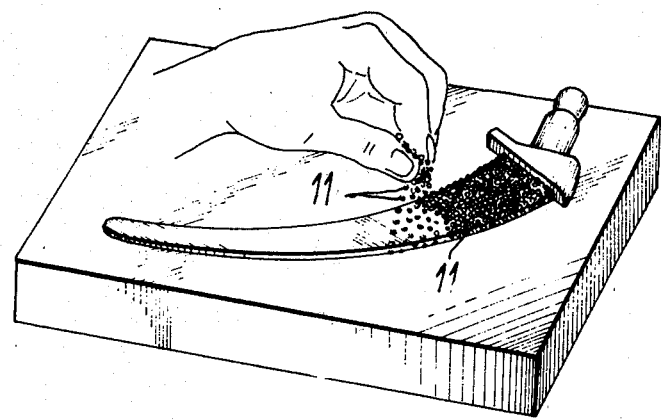
FIG. 4 shows the step of sprinkling balls of plastic material over the surface of the rough pattern.

Then, as seen in FIG. 4, the portion 7 is sprinkled with particles 11, which in the example shown are standard-sized balls of plastic material. In this particular case they are polystyrene balls sold by the firm of Rhone-Progil under the brand name Ascolene, reference "GPE-RH".

The sprinkling may be done by hand, as represented in FIG. 4, or mechanically. Incidentally, it is clear that particles of other materials or forms from those indicated above may be used.

FIG. 4a represents the resulting pattern invested with polystyrene balls 11 adhering to the surface, as shown in enlargement in FIG. 4c, by virtue of the glue as represented in FIG. 4b. In this figure is seen the coating of glue 12 covering the surface 13 of portion 7 of the rough pattern. The balls 11 are in contact with the glue over an area 14 comparatively small but sufficient so that the balls will not come off. This area 14 is of section $S_1$ smaller than the section $S_2$ of the balls at center height.

In this way, it is clearly seen that the interstitial space I between two balls is wider (D) at the layer of glue than at center height of the balls (distance d).

Figure 5:
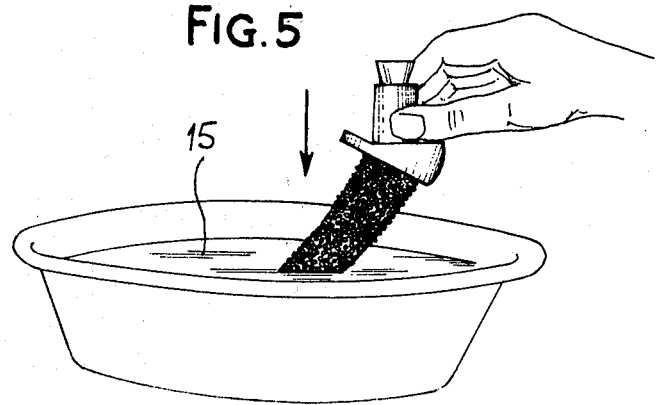
FIG. 5 shows the step of applying the refractory layer to the pattern.

The pattern of FIG. 4a is then coated with a layer of refractory material as seen in FIG. 5. For this operation, a silica-silicate based bath 15 is prepared, in which the pattern of FIG. 4a is dipped. The pattern is then removed from the bath and dusted with silica-silicate in powered form, and the operation several times repeated.

Figure 6:
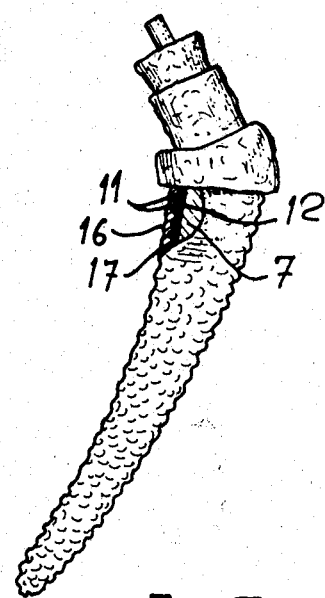
FIG. 6 shows the pattern invested with its refractory layer.
Figure 6A:
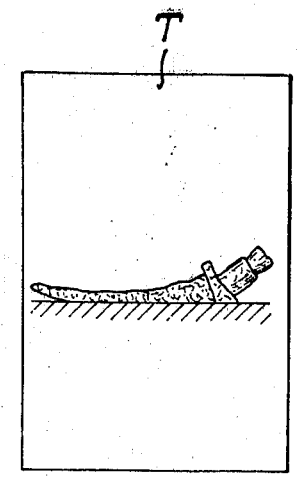
FIG. 6a shows the step of eliminating the pattern by heating to obtain the refractory mold.

The pattern coated with the refractory layer is shown in FIG. 6, in which a partial section has been taken to show the refractory layer 16 perfectly enveloping the rough wax pattern 7 covered with balls 11. The heavy line 17 represents the inner boundary of the refractory layer, which will become the inside wall of the refractory mold 18 (see FIG. 7) obtained after removal of the wax 7, the glue, and the balls 11, by passing the whole through an oven T (see FIG. 6a).

Figure 7:
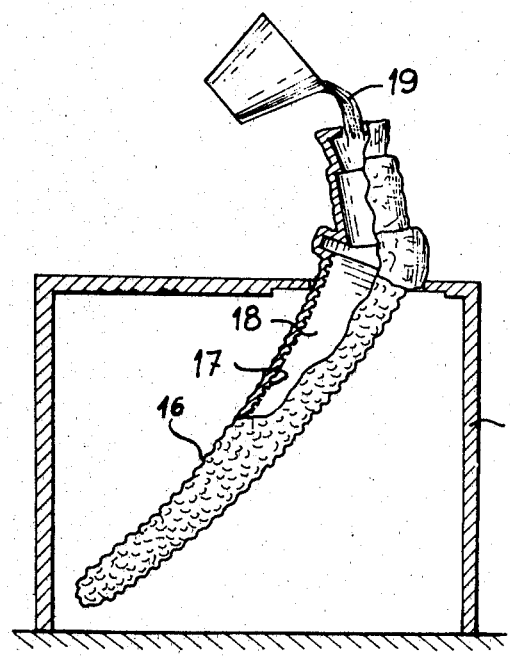
FIG. 7 shows the step of pouring the casting.

In FIG. 7 is seen the refractory mold obtained, in partial section.

The interior space of the mold 18 is bounded by the line 17, a hollow replica of the pattern of FIG. 4a.

FIG. 7 shows the step of casting molten metal alloy 19 in the refractory mold mounted in a fixture P, filling the mold to make the finished part.

Figure 8:
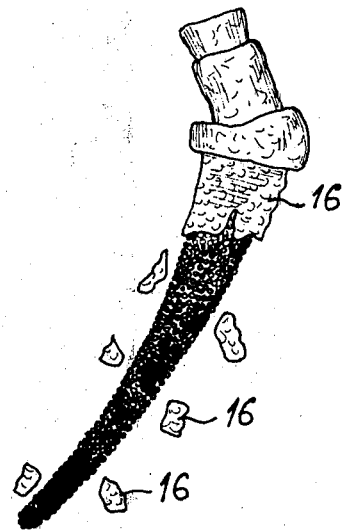
FIG. 8 shows the step of destroying the refractory mold.

After casting, the refractory mold is broken as shown in FIG. 8, and finally the part shown in FIG. 9 is obtained, its stem having a characteristic grainy texture.

FIG. 9a is an enlarged detail of the surface of the stem of the final part, showing the multitude of spherules 20 cast in one piece with the body of the part.

FIG. 9b is a sectional view, to a larger scale, of the surface of the stem. It is seen that the spherules 20 are spaced apart, leaving interstitial spaces I between them reproducing those that were present on the pattern of FIGS. 4a and 4b.

These interstitial spaces have a constriction E substantially at center height of the spherules, and are wider at the surface 21 of the body of the part. Thus it is seen that when bone is reconstituted around the stem of the prosthesis the bony tissue will occupy all the interstitial spaces and lock the prosthesis positively by anchorage of the spherules in the reconstituted bone.

The invention having now been set forth and its usefulness documented by detailed examples, the applicants reserve the exclusive right thereto throughout the term of patent, without limitation other than by the tenor of the claims following.

What is claimed is:

1. A bone prosthesis having a body portion and a grainy multiple planed surface portion comprising a multitude of projections which are approximately in the shape of spherules cast in one piece with the body of the prosthesis from which they project and to which they are directly joined, said projections having interstitial spaces between them with the interstitial space between two neighboring projections being non-uniform throughout the projection height and having at least a constriction at a point intermediate between the body of the prosthesis and the external free end of said projections and said space being not smallest at the base of the projections where attached to the body of the prosthesis.

2. A bone prosthesis having a body portion and surface projections on the body, said prosthesis being adapted to be fixed in a recess in a bone of a human or animal skeleton, the portion of said prosthesis to be placed in the bone recess having a grainy multiple planed outer surface comprising a multiplicity of projections which are approximately in the shape of spherules cast in one piece with the body of the prosthesis form which they project and to which they are directly joined, said projections having interstitial spaces between them for positive anchorage of bony tissue in the prosthesis, with said projections having, on a level intermediate between their base and their summit, an enlarged cross section such that the interstitial space between two adjacent projections has a constriction spaced from the surface of the body of said prosthesis and said projections being joined in said body portion at a seat, said seat having a cross section smaller than the cross section of the projection in a plane parallel to and between said seat and the summit of the projection.

3. A prosthesis according to claim 1 wherein said prosthesis is a joint prosthesis part.

4. A prosthesis according to claim 1 wherein said grainy multiple planed surface is a continuous wrapped around surface.

* * * * *